US007626385B2

(12) United States Patent
Yokoi et al.

(10) Patent No.: US 7,626,385 B2
(45) Date of Patent: Dec. 1, 2009

(54) SYSTEM, METHOD AND APPARATUS FOR MRI MAINTENANCE AND SUPPORT

(75) Inventors: Motohisa Yokoi, Tokyo (JP); Yoshimori Kassai, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 698 days.

(21) Appl. No.: 11/136,422

(22) Filed: May 25, 2005

(65) Prior Publication Data
US 2005/0234330 A1 Oct. 20, 2005

Related U.S. Application Data

(62) Division of application No. 10/328,186, filed on Dec. 26, 2002, now Pat. No. 6,972,565.

(30) Foreign Application Priority Data
Dec. 27, 2001 (JP) ............... 2001-398391

(51) Int. Cl.
 *G01V 3/00* (2006.01)
(52) U.S. Cl. ............... 324/307; 324/309
(58) Field of Classification Search ......... 324/300–322; 600/410–435
See application file for complete search history.

(56) References Cited

U.S. PATENT DOCUMENTS

| 5,551,430 | A | 9/1996 | Blakeley et al. ............. 600/410 |
| 5,708,359 | A | 1/1998 | Gregory et al. ............. 324/309 |
| 6,025,717 | A | 2/2000 | Hertz et al. ............. 324/310 |
| 6,418,334 | B1 | 7/2002 | Unger et al. ............. 600/407 |
| 6,430,428 | B1 | 8/2002 | Lindstedt ............. 600/410 |
| 6,549,009 | B1 | 4/2003 | Hertz et al. ............. 324/309 |
| 6,609,217 | B1 * | 8/2003 | Bonissone et al. ............. 714/26 |
| 6,630,828 | B1 | 10/2003 | Mistretta et al. ............. 324/309 |
| 7,072,931 | B2 * | 7/2006 | Goldhaber et al. ............. 709/201 |

FOREIGN PATENT DOCUMENTS

JP 2001-175762 6/2001

* cited by examiner

*Primary Examiner*—Brij B. Shrivastav
*Assistant Examiner*—Dixomara Vargas
(74) *Attorney, Agent, or Firm*—Nixon & Vanderhye, PC

(57) ABSTRACT

An MRI apparatus consolidates and stores maintenance and/or performance data automatically measured by a measurement unit and data manually input via an input device. The automatically measured data may include an adjustment value, a state value or an error record. The manually input data may include a software and/or hardware upgrade record, a customized situation record, a network connection record, a repair record, a check record, a maintenance record or an installation record, for example. Both types of data can be obtained swiftly and faults or malfunctions can be recovered from quickly or even prevented in advance. The stored data may be communicated among a plurality of MRI apparatuses, a service center apparatus and a maintenance support apparatus via a communications network.

5 Claims, 6 Drawing Sheets

SYSTEM, METHOD AND APPARATUS FOR MRI MAINTENANCE AND SUPPORT

CROSS-REFERENCE TO RELATED APPLICATIONS

This application is a division of U.S. patent application Ser. No. 10/328,186, filed Dec. 26, 2002 now U.S. Pat. No. 6,972,565, the entire content of which is hereby incorporated by reference in this application.

BACKGROUND OF THE INVENTION

The present invention relates to a system, method and apparatus for providing maintenance and support for a magnetic resonance imaging (MRI) apparatus. In particular, the present invention is directed to a method, system and apparatus for providing preventative maintenance for MRI apparatuses, for quickly and efficiently diagnosing faults in an MRI apparatus, and for efficiently repairing faulty MRI apparatuses.

Typically, a service log related to an MRI apparatus, such as a repair log and/or a performance/maintenance check log, is stored separately by a service provider and a customer. This log is used for various kinds of investigations, such as, for example, to find a cause of a fault that occurs in the MRI apparatus. When a fault is detected, the composition of circuit boards in the MRI apparatus is checked, the various parameters that may have been adjusted when the apparatus was installed are measured, and a cause for the fault and a malfunctioning part are pinpointed based on information contained in a maintenance manual. The result of a scheduled or routine maintenance check may be useful in many cases in determining the cause of the fault and the suspected malfunctioning part. However, because the results of such checks or routine maintenance are not stored in the MRI apparatus, and are retained in separate locations, it is difficult to access these service logs and to provide service quickly and efficiently.

There are many different kinds and types of imaging methods that can be employed in a conventional MRI apparatus. Certain special imaging methods, such as FASE and EPI, are not used frequently because they are reserved for specific diagnosis. On the other hand, general imaging methods, such as SE and FSE, are used frequently because they are used for routine diagnosis (T1, T2 and 3DMRA, etc.). It is difficult to recognize and determine degradation of the MRI apparatus by merely viewing images obtained by the general imaging methods (SE, FSE, etc.), as compared with also viewing images obtained using specialized imaging techniques such as those mentioned above (FASE, EPI, etc.) which exercise a larger range of performance of the apparatus. Therefore, even if an image actually indicates some degree of degradation, it is difficult to determine when or where the degradation of the malfunctioning part started.

Some pulse sequences that are sensitive to the condition of the apparatus are mentioned below.

(1) FSE (ETS more than 15 ms) is sensitive to the state of an eddy current, and it manifests itself as non-homogeneous sensitivity in the image and as variable signal strength in different image slices.

(2) FE-EPI is very sensitive to gradient magnetic field stability, especially offset fluctuation of the gradient magnetic field amplifier, and if there is instability, it manifests itself in the image.

(3) A fat reduction pulse sequence is sensitive to homogeneity of the magnetic field and the remains of eddy currents, and it clearly appears as uneven fat tissue indications in the image.

(4) A spin-labelling pulse sequence for perfusion imaging is sensitive to RF magnetic field stability because it measures a difference at the step of an addition average according to the generating pattern of the RF pulse, and it appears in the Signal to Noise Ratio (SNR).

There are also failure and degradation conditions of the apparatus which do not affect the quality of the image directly. In that case, it is time consuming and labor intensive to determine whether the fault or degradation conditions occurred suddenly or gradually. It is also difficult to gather related information.

In clinical inspection, it is rare that RF signals are received on one Whole Body (WB) coil. Typically, a plurality of different RF coils are used depending upon the part of the body being examined. Some of these RF coils, for example, those used for the shoulders and for knees, are not used frequently. Because of their infrequent use, the operational condition of these coils, such as achievable SNR, is not always clear because they are not checked or observed on a regular basis. Thus, the determination that they are out of order typically occurs in an untimely manner.

As mentioned above, the service log is stored at a service provider and a customer site separately, thus people who require the information contained in the service log must contact the service provider site where it is kept. Therefore, in order to ascertain the repair history and performance check history, or to determine which upgrades or accessories have been included with a particular MRI apparatus, each of these inquiries must be accomplished separately.

Since an MRI apparatus includes many different constituent units, it is difficult to confirm the part, start time and grade of malfunction when an imaging fault occurs under, for example, specific image conditions. Therefore, achieving repair becomes time consuming and inefficient. In addition, because all log data regarding each apparatus is not consolidated, it becomes particularly burdensome to statistically manage and upgrade the MRI apparatuses.

Under such conditions, for example, the following problems may occur.

(a) No one may notice that a serviceman may repair the apparatus according to incomplete or incorrect information.

(b) Since the serviceman repairs only according to the manual, it may take considerable time to confirm new troubles which are not described in the manual.

(c) It is difficult to compare the diagnostic check results of the apparatuses and analyze them to determine a trend of faults or malfunctions.

(d) Because it is difficult to confirm the upgrade record, the serviceman cannot serve the customer according to the conditions peculiar to each apparatus.

(e) If the conditions of the apparatus are such that there is the possibility of an accident or harm to a patient, no one may be alerted to the condition or notice the condition in a timely manner.

(f) It may take considerable time to exchange the units, because an order for exchange flows by way of the service provider. Exchange orders originate from the customer and are sent to a maintenance center via the service provider, and exchanges are sent directly from the maintenance center to the customer.

SUMMARY OF THE INVENTION

It is an object of the present invention to minimize the time associated with an investigation to determine the condition of the apparatus as much as possible, accelerate the dispatch of repair units, and repair the apparatus swiftly. Additionally, it is preferable to determine whether the trouble occurred suddenly or gradually according to the service log, and to make this determination accurately. Moreover it is preferable to anticipate long-term or middle-term troubles at an early stage by recognizing degradation of the apparatus according to results of diagnostic checks, and to prevent future system failures.

According to a first exemplary aspect of the present invention, an MRI apparatus comprises a main unit configured to generate a radiofrequency magnetic field and receive magnetic resonance signals from an object, a measurement unit configured to automatically measure at least one of an adjustment value, a state value and an error record of the main unit, an input device configured to manually input at least one of a software and hardware upgrade record, a customized situation record, a network connection record, a repair record, a check record, a maintenance record and an installation record, and a memory unit configured to consolidate and store measured data from the measurement unit and the input data with the operation unit.

According to a second exemplary aspect of the present invention, an MRI apparatus comprises a main unit configured to generate a radiofrequency magnetic field and receive magnetic resonance signals from an object, a memory unit configured to store a schedule of diagnostic imaging to check the main unit of the MRI apparatus and a controller configured to direct the operator to prepare diagnostic imaging according to a schedule.

According to another aspect of the present invention, an MRI apparatus comprises a main unit of the MRI apparatus configured to generate a radiofrequency magnetic field and receive magnetic resonance signals from an object, a memory unit configured to store a schedule of a plurality of imaging methods by which to check the main unit of the MRI apparatus and a controller configured to inform the operator of a phantom used for a particular imaging technique and to direct the operator to prepare the imaging according to the schedule.

According to another aspect of the present invention, a maintenance support apparatus is connected to a plurality of MRI apparatuses and comprises a communication unit configured to communicate with the MRI apparatus via a communication network, a memory unit configured to store at least one of an adjustment value, an state value, an error record, a software and hardware upgrade record, a customized situation record, a network connection record, a repair record, a check record, a maintenance record and an installation record and a controller configured to search data from data stored in the memory unit according to the request from the MRI apparatus and send the searched data to the MRI apparatus via the communication unit.

Therefore, both automatically measured data and manually input data can be obtained swiftly and faults can be recovered quickly or prevented in advance.

BRIEF DESCRIPTION OF THE DRAWINGS

The invention will be described in detail herein with reference to the following drawings in which like reference numerals refer to like elements, and wherein.

DETAILED DESCRIPTION OF EXEMPLARY EMBODIMENTS

Figure 1:
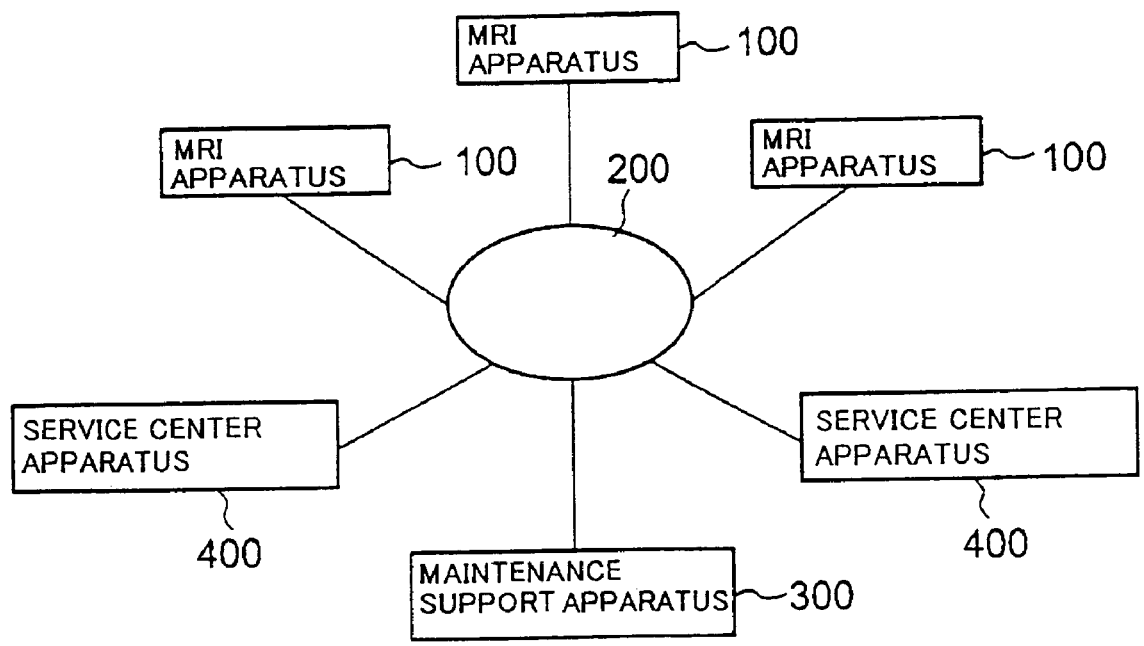
FIG. 1 is a block diagram showing a maintenance support system.

With reference to drawings, an exemplary embodiment of the invention will be described herein. FIG. 1 is a block diagram showing a maintenance support system. In this figure, a plurality of MRI apparatuses 100 are connected to a maintenance support apparatus 300 via a communication network 200, such as, for example, a general public line or a dedicated line. In addition, a plurality of service center apparatuses 400 are also connected to the maintenance support apparatus 300 via the communication network 200.

The maintenance support apparatus 300 stores data about each MRI apparatus 100. The data relates to all or at least one of adjustment, state of each part, repair, maintenance, check, software and hardware upgrade, software customizing, error, the conditions at the installation, the building construction and the network connection. The apparatus 300 sends information to the MRI apparatus 100 or the service center apparatus 400 as necessary. Thus the information stored cumulatively is useful and easily accessible at the time various work takes place, such as, for example, maintenance, repair, and upgrade (renewal and/or addition of a function). The information history record is hereinafter referred to as apparatus chart information.

The maintenance support apparatus 300 may function as a server, and the MRI apparatus 100 and the service center apparatus 400 which may function as clients receive the apparatus chart information from the maintenance support apparatus 300 as requested or in the case of various work described above.

Figure 2:
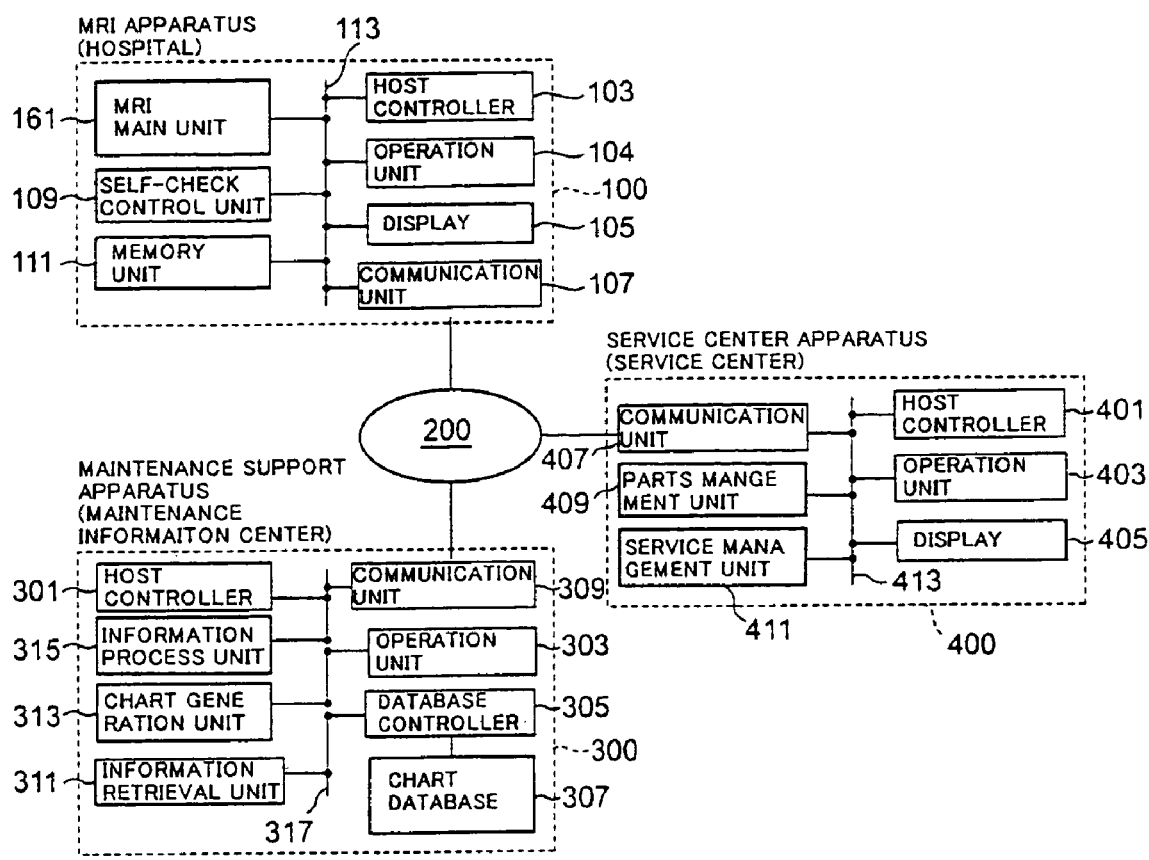
FIG. 2 is a block diagram showing an MRI apparatus, a maintenance support apparatus, and a service center apparatus.

The MRI apparatus 100, the maintenance support apparatus 300, and the service center apparatus 400 are shown in detail in FIG. 2.

The MRI apparatus 100 includes a main unit 161 which includes magnetic coil assemblies, a computer, etc. The main unit 161 collects RF signals and reconstructs images. A host controller 103 is connected to the main unit 161 via a data control bus 113.

An operation unit 104, a display 105, a communication unit 107 for communicating with the maintenance support apparatus 300 via the electronic communication network 200, a self-check control unit 109 for periodically performing a self-check program, operating the main unit 161 and checking a state of main unit 161, and a memory unit 111 which stores the information about the state, are connected with each other via the data control bus 113.

The maintenance support apparatus 300 includes a host controller 301. A communication unit 309 and an operation unit 303 of the maintenance support apparatus 300 are connected to each other via data control bus 317. In addition, the apparatus 300 includes a chart generation unit 313 generating the apparatus chart information based on the transmitted information from a plurality of MRI apparatuses 100 in a contract group or the service center apparatus 400, a chart database 307 consolidating and storing the apparatus chart information, and a database controller 305 controlling the chart database 307. The apparatus 300 may also include, an information retrieval unit 311 which retrieves useful information in the chart database 307 responding to a demand from the MRI apparatus 100 or the service center apparatus 400 and an information processing unit 315 which statistically processes the apparatus chart information read from the database 307 as service to the MRI apparatus 100 or the service center apparatus 400.

The service center apparatus 400, placed in a service center for providing various services to the MRI apparatus 100, such as maintenance and repair, has a parts management unit 409 which manages required parts purchase, stock, conveyance, etc. and a service management unit 411 which manages a schedule for a serviceman, remote maintenance staff, and manages the content of an actual maintenance, repair etc.

Next, an exemplary apparatus chart information will be described. The information may include the following various record items described below. Although these items are classified in the categories described below, all items are consolidated and stored together as apparatus chart information.

The various adjustment values of the MRI apparatus 100 (RF adjustment value, pulse sequence adjustment value, magnetic uniformity adjustment value, etc.)

The state values of the MRI apparatus 100 (temperature value of each part, voltage value of each part, residual value of liquid helium, surrounding temperature, amount of cooling water, etc.)

The repair record of the MRI apparatus 100 (circuit board exchange, its serial number, etc.)

The maintenance record of the MRI apparatus 100 (charge of the liquid helium, each part overhaul, etc.)

The check record of the MRI apparatus 100 (result of a scheduled check, etc.)

The software and hardware upgrade record (version record of the software, a type of hardware options, etc.)

The customized situation record (customizing the software, etc.)

The error record (problems, the contents of correspondence, images and parameters at the time of the trouble (however it will be understood that this record shall include a mechanism in which all the information that specifies a particular patient or patient's information are deleted automatically from the viewpoint of privacy protection of the patient))

The installation record (date of the installation, SNR, trouble generated, worker's name, building construction record (a shield room sketch, a cold-water piping course figure, a power supply construction course figure, other special construction data), etc.)

The network connection record (connection place, connection time, download classification, etc.)

At least four items of the higher ranks of a list (the various adjustment values, the state values, the repair record and the maintenance record) can be published not only to user who owns the apparatus to which the items relate but also to other users. In order to preserve this published information, the published information cannot be changed. Accordingly, a record medium or process that prevents such overwriting of data may be used.

The information retrieval unit 311 of the maintenance support apparatus 300 enables reference to the past apparatus chart information of the MRI apparatus 100 that provided it and similar example reference of other MRI apparatuses 100.

The maintenance support apparatus 300 provides communication functions (e-mail etc.) with a user (the MRI apparatus 100, the service center apparatus 400). According to a request for reference check or adjustment data from the user, the information processing unit 315 in the maintenance support apparatus 300 may change a normal format of the apparatus chart information to a statistical format, such as, for example, a graph, so that a user who is familiar to the apparatus can more quickly and easily understand the situation. Other information where the format can be changed include, for example, temperature data trend graph, LHe attenuation graph, a magnetic field attenuation graph, a comparison graph with the other apparatus of the adjustment value, etc.

Next, the category of each of the items of the apparatus chart information will be described. The items are categorized according to an input method. One is input manually by the operator and the other is input automatically by the apparatus. Additionally, manual input categories may be classified into a more detailed categories. For example, one is input periodically or only once and the other is input selectively (e.g., on an irregular basis).

The automatically stored items may include, for example, various adjustment values (RF adjustment value, pulse sequence adjustment value, magnetic uniformity adjustment value, etc.), the state values (temperature value of each part, voltage value of each part, residual value of liquid helium, etc.) and error record data (problems, the contents of correspondence, images and parameters at the time of the trouble).

The manually stored items that are input selectively, may include, for example, the software and hardware upgrade record, the customized situation record, the network connection record, the repair record (circuit board exchange, serial number, RF coil exchange, etc.). The circuit board exchange data may be stored automatically if the circuit board has a ROM where identification (ID) number is recorded. In addition, a serial number bar code may be pasted on the RF coil.

The manually stored items input periodically or only once may include, for example, the check record, the maintenance record and the installation record.

Each item of the apparatus chart information can be referred by the service center apparatus 400 through the communication network 200. The maintenance support apparatus 300 can provide the information as a printout, if necessary. The information is consolidated, classified and used, for example, as set forth below.

Repair and error record: A third person (e.g., a service specialist) can confirm the validity of the repair immediately. Therefore, it becomes easy to find a repair mistake and prevent a failure expansion after the mistake occurs. If the error record is used with other records such as the state values of the MRI apparatus 100, efficient troubleshooting can be performed. Furthermore, since the MRI apparatus 100 and the service center apparatus 400 are connected via the communication network 200, when an accident occurs with the MRI apparatus 100, the service specialist can access the newest information stored in the maintenance support apparatus 300 and repair the MRI apparatus 100. When a complicated accident occurs, other service specialists can assist using the shared information.

If the serious accident that involves a patient, the alert is sent to the MRI apparatus 100 from the service center apparatus 400, and a user receives notice of the alert. As soon as the report to the government is completed, the same alert is sent to other MRI apparatuses as recall (manual operation or automatically) information, such as readjustment, parts exchange and handling warning. In this manner, similar accidents may be prevented.

Maintenance record: In order to maintain the MRI apparatus efficiently, it is necessary to document the current state of the MRI apparatus. Basic data for this is a performance index parameter (an eddy current, T2*, etc.) obtained by the scheduled check described below. Maintenance is indicated when the value of these index data exceeds a standard value, fluctuates in comparison with the stored previous value or tends to be an unusual value, such as tending upward or downward. For example, because a vacuum tube of a RF amplifier does not usually break suddenly (rather its output typically declines gradually) it may be adjusted according to the trend of the value of the transmitting gain by imaging a phantom. If the number of adjustment times is stored, system breakdown can be prevented by exchanging the vacuum tube before imaging is made impossible by vacuum tube failure, for example.

As another example, if the apparatus chart information including internal information and external information is similar to apparatus chart information of another MRI apparatus that has been adjusted, the MRI apparatus may be adjusted in the same or similar manner as the other MRI apparatus. Moreover, the software may be upgraded on basis of the apparatus chart information of an MRI apparatus that is broken.

State values and adjustment values: All of the state values of the MRI apparatus 100, such as temperature value of each part, are fed to the information processing unit 315, and as the result, the trend data and the comparison data with other apparatuses are utilized with the service center apparatus 400. This process may be done automatically.

By analyzing trend data, it is possible to request parts exchange when the check value changes or to predict degradation and accident. Moreover, by analyzing the comparison data, it is possible to find an unusual use environment or discover better adjustment values that improve the performance of the apparatus 100. For example, the residual quantity of liquid helium for cooling a superconducting magnet is measured by the apparatus 100 automatically every day, and the measured value is fed to the maintenance support apparatus 300. It is possible to calculate the date when the liquid helium should be filled from the measured values and to report it to a service provider or a user in advance. Thus, an appropriate service schedule can be achieved. For example, the residual quantity of the liquid helium is attenuated 10% in the first month after a supplement and 20% in the second month, and if the cooling is in a dangerous state when it becomes 40% or less, the liquid helium should be filled before the fourth month. As another example, the freezer for cooling a superconducting magnet has mechanical parts, and it has to be repaired periodically. Although there is a rough estimate of the life of such parts, it changes somewhat with operating conditions of apparatus. If such mechanisms are repaired after breaking down, the apparatus cannot be used until repaired. From the user's perspective, it may cause serious and unexpected damage or delays. If it is repaired too early, a repair term becomes too short resulting in inefficient and expensive operation. Therefore, because it is clear that the reduction of the capability of the freezer is influenced by an increase of temperature, the temperature value is measured periodically and automatically. Consequently it is possible to determine a suitable repair schedule from the periodically measured values as set forth above.

Upgrade, installation, customized situation, network connection: these items are stored as a particular log. Since similar examples can be found, they can be utilized for preventing accidents in new installations and for upgrades. Additionally, other items which were realized during the installation and the upgrade are also recorded.

With respect to the building construction record, when, for example, unusual special work, such as carrying the apparatus on the top floor of a 20 floor building with a special crane is required, there may be many attendant problems, including, for example, legal investigation in the case of using the special crane and examination of the circulation height difference of cooling water are necessary, for example. These problems and the contents of correspondence, notes, etc. are stored as a particular log. For example, before cold-water system maintenance etc., a worker can confirm the procedure of shutting a valve with reference to this particular log. When a similar situation occurs subsequently, the notes about the prior special work can be checked in detail by analyzing this particular log in the maintenance center.

As another example, since MRI apparatus are extremely expensive, they cannot be purchased or replaced frequently. Thus, various hardware and software upgrades are typically performed in order to improve performance. If an upgrade record is not stored, adverse consequences may result from lack of knowledge of previous upgrades when a subsequent upgrade occurs or is scheduled. On the other hand, if an upgrade record is stored, problems can be anticipated and avoided. For example, when software is upgraded, the load on certain hardware, e.g. the CPU, increases. Hence, if software is upgraded frequently without confirmation of hardware state, it may become impossible to secure the required speed of operation during clinical use.

Check record: As explained above, there are some cases in which degradation of the MRI apparatus 100 can be found only by using a specific pulse sequence. Therefore, the basic degradation data of the MRI apparatus can be obtained using the specific pulse sequence. When a measured value using the specific pulse sequence is unusual, or is within an acceptable range, but tends toward being unusual, an alert is generated and the procedure for repair is started based on this measurement.

Figure 6:
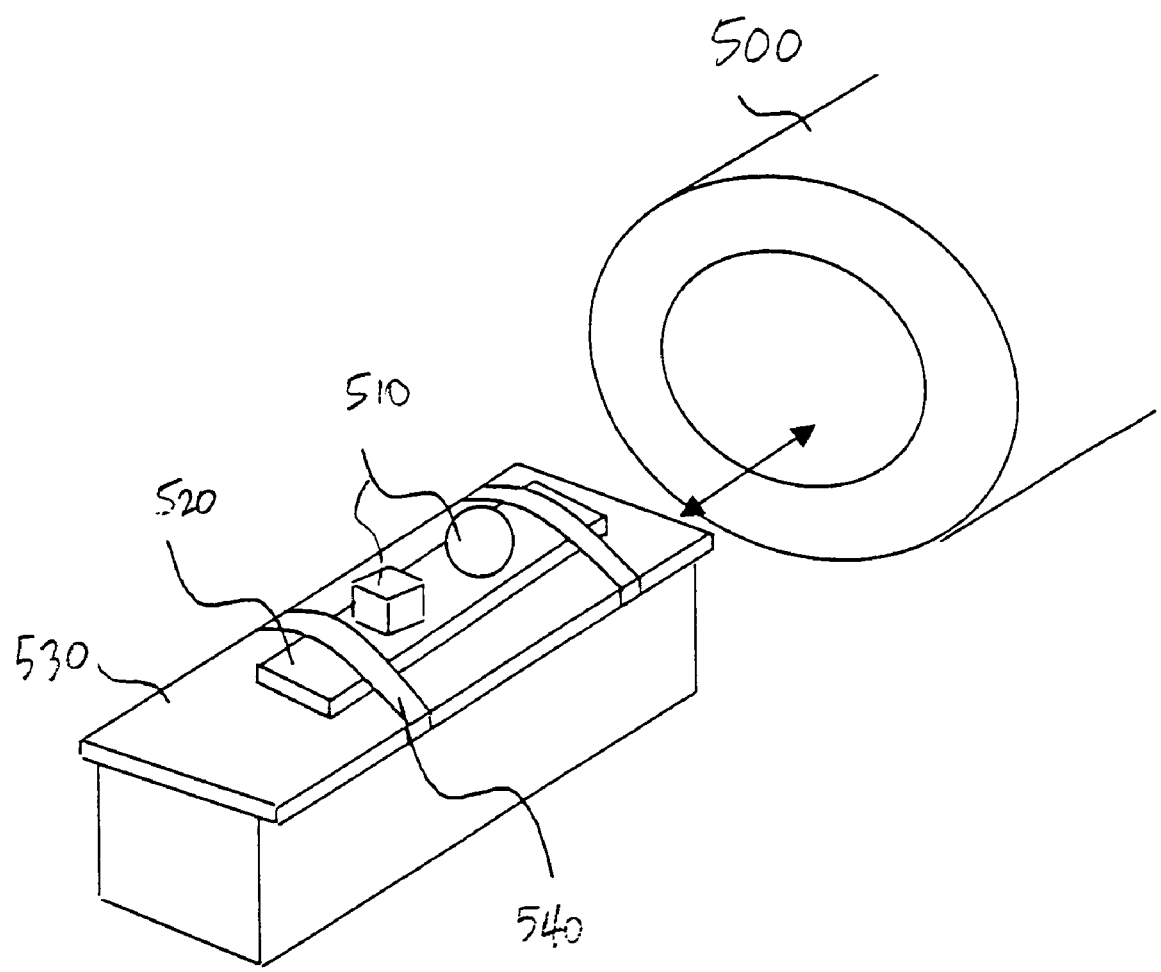
FIG. 6 is an illustrative diagram showing phantoms used for measuring performance of the MRI apparatus.

Before the performance index parameter measured is described, a phantom and the scheduling software themselves are described below. FIG. 6 is an illustrative diagram showing, for example, a plurality of phantoms 510 arranged on a phantom rest 520 for measurement by the MRI apparatus. The phantom rest 520 is arranged on a bed 530 and is secured thereto by, for example, belts 540. The phantom rest 520 is then introduced to the MRI apparatus via the MRI gantry 500. Of course, it will be understood that only one phantom or a plurality of phantoms may be used depending upon the measurement being made. There are many pulse sequences, one of which shortens a total imaging time by shortening a repetition time interval (TR) and another of which obtains a large signal by extending TR, such as, for example, FSE. A phantom material that is adequate appropriate for T1 enhancement image is one that has a long T1 relaxation time and outputs a large signal easily with short TR, such as, for example, oil. While, a phantom material that is appropriate for a T2 enhancement image is one that has a long T2 relaxation time, such as, for example, water. In addition, in order to measure the uniformity of the static magnetic field, a spherical phantom which does not disturb a magnetic field is required. Thus, automatic measurement may not work using only one phantom. An appropriate phantom is selected and communicated to an operator at the end of a day by the scheduling software. The selected phantom may be one phantom or a plurality of phantoms. If using a plurality of phantoms, such as, for example, shown in FIG. 6, a phantom rest 520 where the phantoms 510 are arranged with the distance between phantoms of about 50-70 cm which can separate a sensitive range of the WB coil may be used. The phantom rest 520 is laid on the bed 530 and moved automatically. As mentioned above, the phantoms 510 are preferably arranged such that their signals do not interfere with one anther. The phantom rest 520 may also include indentations or dimples (not shown) along a central axis thereof to prevent the phantoms 510 from falling off the rest 520 during measurement. The phantom data is then collected according to the protocol of the scheduling software. When the end of a measurement day comes, the scheduling software informs the operator and requests measurement preparation.

Next, the performance index parameter measured for the apparatus chart information will be described according to the types of te measurement intervals. For example, there may be three types, one of which is measured every time before use (every day), another of which is measured every week and another of which is measured every month. Each data is measured according to the scheduling software. The data is stored in the MRI apparatus 100 and also in the maintenance support apparatus 300.

An example of data that is measured every day or every other day is data of a standard picture containing SNR of the WB coil. This measurement is used to check operation of the WB coil itself and the whole system, including transceiver function. This measurement is generally performed by the user every day. The measurement includes obtaining, SNR, signal value, noise value, the main frequency of a magnetic field, the transceiver gain of RF system, the stability of gradient magnetic field, etc. The measurement typically takes about 1 minute, using a phantom, such as, for example, mineral oil, whose T1 term is short. SNR is a parameter by which the state of the whole system can be checked synthetically. If SNR is less than the usual value, repair and adjustment are required immediately. In addition, when SNR is unusual as described above, the main cause can be immediately determined by referring to the signal value, noise value, the main frequency of a magnetic field, and the transceiver gain of RF system. The above signal value is a value of SNR and may indicate a signal value on the reconstructed image of the phantom or a signal value before reconstruction.

The above signal value divided by the receiving gain of RF system is an actual signal value. The signal value typically changes when there is a failure and/or degradation of RF transmitting system, receiving system and/or degradation of the WB coil. The above noise value is a value of SNR and may indicate a noise value on the reconstructed image of the phantom or a noise value before reconstruction. The above noise value divided by the receiving gain of RF system is an actual signal value. This noise value is not influenced by failure and degradation of RF transmitting system but is changed by the receiving system and degradation of the WB coil.

The transmitting gain of the above transceiver gain of the RF system is a parameter which is used for determining the amount of RF transmission. When this value is large, RF electric power supplied to a patient is large, and when small, supplied RF electric power is small. RF electric power is fixed using the regular phantom which is checked every day. The transceiver gain should be changed according to bodily shape and weight of the patient. Failure and degradation of RF transmitting system can be detected by this change. The receiving gain of the transceiver of the RF system is measured from the signal value of the patient indirectly. Failure and degradation of RF receiving system (besides degradation of a receiving coil itself can be found from the signal value, while failure and degradation of RF transmitting system may be obtained using a certain regular phantom whose characteristics are known.

The above-noted main frequency of a magnetic field is a magnetic resonance frequency at the center of the static magnetic field. The intensity of the static magnetic field can be calculated by Larmor equation based on the main frequency of a magnetic field. In general, a magnetic material (e.g., iron etc.) is used for a magnetic field and a magnetic circuit. The intensity of the static magnetic field changes according to the temperature of the magnetic material. When a superconductive magnet is used, the magnetic field decreases gradually over time. The stability and the uniformity of the static magnetic field are very important parameters in improving quality of an MRI image. If a small magnetic object, such as a ballpoint pen, is near the MRI apparatus, or a large magnetic object, such as a car, is near an MRI room, it is possible for the main frequency to change discontinuously. In these cases, there is a strong possibility that the quality of the image will be degraded, and the cause of this degradation should be identified and removed immediately. When image quality degrades, and there is no record of the main frequency of the magnetic field, finding the cause becomes both time consuming and labor intensive.

It is possible to measure SNR from not only a phantom image using the WB coil as explained above, but also from a patient image using other coils. Accordingly, the SNR of other coils may measured without great effort. For example, the first patient is imaged by using the RF coil under the condition that RF output is zero in order to measure a noise of the RF coil itself, and a locater (scout) image is obtained. The locater image is used for locating Field of View (FOV), but is not used directly for diagnosis. The FOV and other parameters may be fixed in order to shorten imaging time. Next, the image of the FOV is obtained. Its signal (a fat signal obtained automatically from a fat tissue near a body surface, for example) and the above-mentioned zero RF output noise are used to measure SNR. The noise may be obtained by subtracting two independent images instead of the above-mentioned zero RF output method. In these measurements, not only SNR but also the transmitting gain, the receiving gain and reflective ratio of RF amplifier may be obtained and stored in the apparatus chart information.

Examples of data that are measured every week by the scheduling software are described in further detail below.

One example is eddy current data. In this measurement, a square shaped phantom, for example, including oil is required. The eddy current is a harmful current generated by electromagnetic induction of a metal near the MRI apparatus based on switching of the gradient magnetic field. The main cause is the magnetic leakage from a gradient coil which generates gradient magnetic field. In recent years, the amount of leakage has been decreasing due to use of an active shield gradient coil. However, the amount of leakage is not zero, and may be adjusted. The eddy current of the conventional MRI apparatus is adjusted along nine axes, X-X, X-Y, X-Z, Y-X, Y-Y, Y-Z, Z-X, Z-Y, and Z-Z, and it decreases less than $\frac{1}{10}$ to $\frac{1}{100}$ in comparison with installation time. However, even in such a case, it turns out that the measured value becomes unstable due to failure of a gradient coil or its power supply, and the resulting eddy current increases. Therefore, short-term stability of the eddy current is obtained by measuring it many times in one night, and its long-term stability is obtained from a plurality of past records that may be checked. Thus, the stability of the eddy current may be readjusted periodically, such as, for example, every week. Since one measurement and adjustment takes about 10 minutes, it is possible to measure and adjust the eddy current automatically many times in one night.

Another example of weekly data is adjustment of the gradient magnetic field. In this measurement, a square shaped phantom including oil, for example, is required. This adjustment includes adjustment of the intensity and the waveform characteristic of the gradient magnetic field. In the measurement of the intensity of gradient magnetic field, a cube phantom, for example, whose side length is accurately known in advance, is placed such that each side is parallel to X, Y and Z-axis respectively. In this situation, the phantom is imaged and the side length is calculated on the basis of the projection data from each direction. The intensity of gradient magnetic field is adjusted such that the calculated side length is close to the side length known in advance.

The waveform characteristic adjustment of the gradient magnetic field is used to correct the amount of distortion at changing points, such as, for example, a standup point of an gradient magnetic field. The fluctuation of gradient magnetic field is measured from a signal (a signal and phase information) of the phantom, then the amount of distortion is compensated. Unless these adjustments are made correctly, the FSE adjustment, EPI delay time adjustment, and FE-EPI time stability investigation cannot be correct.

Another example of weekly data is FSE adjustment value. In this measurement, a square shaped phantom including oil or water, for example, is required. FSE stands for Fast Spin Echo which is a type of pulse sequence. In FSE method, it is important to control the phase of the repeated echo signal. The FSE adjustment value is evaluated synthetically from the delay time of gradient magnetic field system by the eddy current and the delay time of RF system, etc. This FSE adjustment value includes one value which is relative to the frequency of a multi-slice and another value which is independent of the frequency, namely the offset value. These values are expressed as a phase and a phase/frequency, respectively. Since this parameter detects small error by a phase value, it is mainly used for checking failure of the RF system.

Another example of weekly data is shimming adjustment value. In this measurement, a phantom including water, for example, is required. The shimming adjustment indicates uniformity adjustment of the static magnetic field intensity. The uniformity changes based on various factors. For example, a change in room layout, small magnetic material carried into the room by a patient or an operator, such as, for example, paper clips, that stick to the apparatus, a change in the output of a gradient magnetic field power supply or a shimming power supply, or degradation of a shimming coil or a gradient coil, for example. Since there are many factors affecting uniformity of the static magnetic field intensity, such as those mentioned above, it is difficult to find the actual cause of any non-uniformity, but it is possible to narrow down the likely causes by storing periodic data together with the value of the above-mentioned main frequency.

Another example of weekly data is EPI delay time adjustment value. In this measurement, the phantom is not especially limited. EPI stands for Echo Plainer Imaging. In EPI, a signal is obtained repeatedly by a gradient pulse changing at positive/negative after transmitting RF pulse to a patient. The delay time of the echo peak Even/Odd of EPI is generated by output distortion of a gradient magnetic field power supply and the eddy current, especially short-term eddy current caused by RF shield. The EPI delay time can be adjusted by changing RF output timing.

Another example of weekly data is FE-EPI time stability value. In this measurement, the phantom shape is not especially limited, but the material inside the phantom must be water. FE-EPI time stability value is evaluated by dynamic study where the same position images of a phantom are repeatedly obtained at predetermined intervals. The level of N/2 artifacts is measured at two or more points. Failure of a gradient magnetic field power supply and a gradient coil, and RF shield peeled off, etc. can be detected using this data.

Yet another example of weekly data is ghost value. In this measurement, the phantom shape is not especially limited and the material inside the phantom may be water or oil. The ghost value is defined as an artifact of the scatter signal to the encoding direction in the background of a reconstructed image.

Another example of weekly data is a pair of T1 enhancement image (SE) and T2 enhancement image. An artifact of the T1 image is different from an artifact of the T2 image. In order to obtain a large signal, in T1 imaging, an oil phantom should be used, and in T2 imaging, a water phantom is desirable. Since it is difficult to find a cause at only one measurement, these images must be stored.

If it takes a long time to measure a combination of the above-mentioned weekly parameters, the parameters may be measured monthly. In monthly measurement, as in the weekly measurement, when a measurement day comes, the scheduling software confirms and at the end of a day, notifies the operator and requests measurement preparation. The remainder of the monthly procedures are the same as or similar to that of the weekly measurement.

Figure 3:
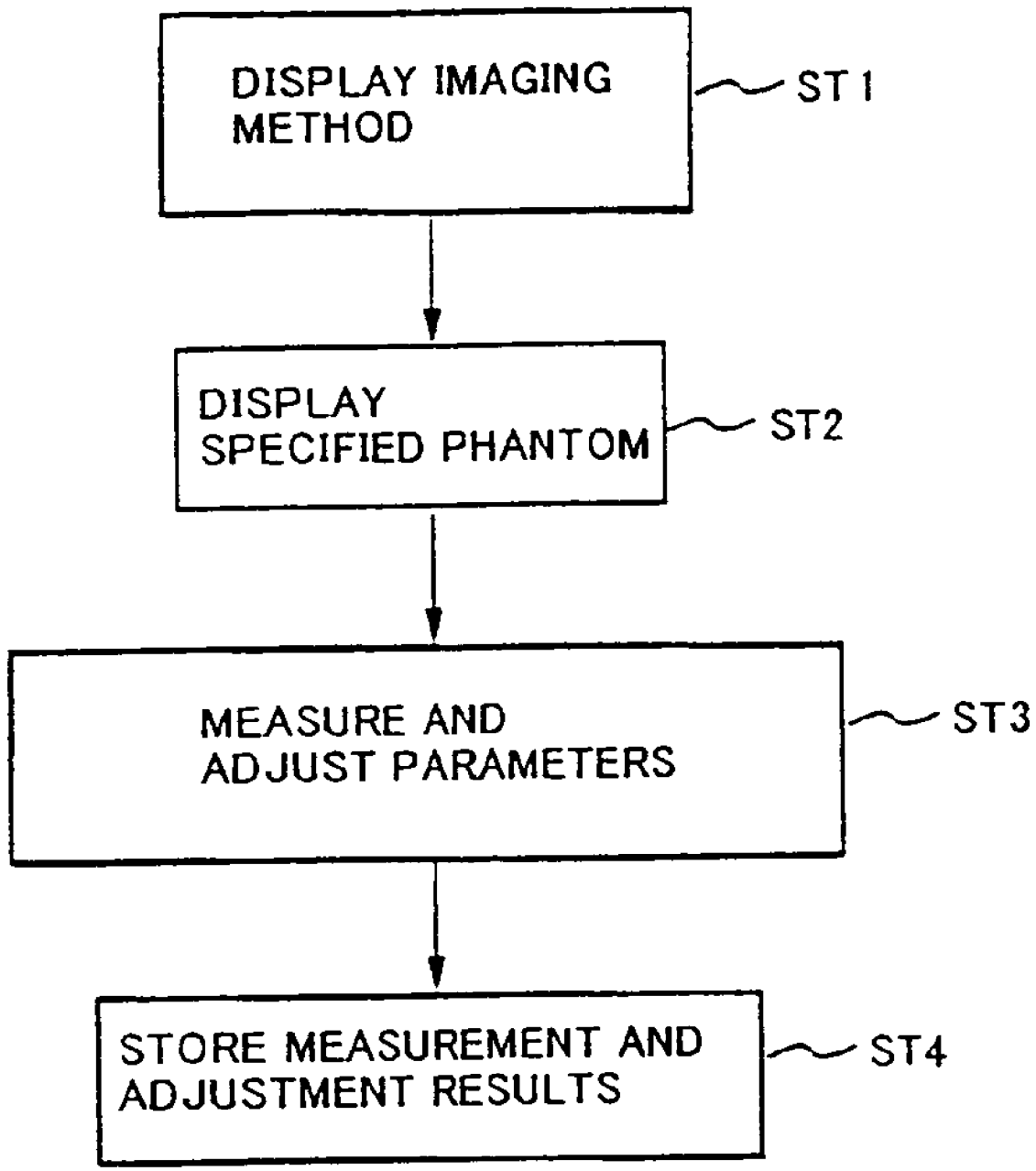
FIG. 3 is a flow chart illustrating an exemplary procedure for a scheduled maintenance or performance check of the MRI apparatus.

The operation of this exemplary embodiment will be described below as a scheduled check with reference to FIG. 2 and FIG. 3. Since the operating frequency of a coil or a pulse sequence differs in each hospital, the scheduled check menu is created according to the operating conditions of a particular unit. For example, in a hospital of cranial neurosurgery where the operating frequency of the WB coil is low, the scheduled check menu is created such that SNR is measured with a head coil every day, while SNR of the WB coil is measured weekly. Thus, the check of the head coil is more frequent, and a fault can be found early. The scheduled check menu is stored in the self-check control unit 109 of each MRI apparatus 100 as a part of the scheduling software.

The software stored in the self-check control unit 109 recognizes the end of the day when the measurement is planned by, for example, detecting an off-command operation by the operator, such as shutdown via the operation unit 104. Such a notification including a type of imaging method is displayed on the display 105 in step 1. The specified phantom corresponding to the imaging method is also displayed on the display 105 in step 2. After the operator completes preparation, phantom imaging starts using a specified imaging method, parameters of the system are automatically measured and adjusted by the software in step 3. As mentioned above, if the phantom rest which moves automatically is used, the operator may not wait during the phantom imaging, and automatic measurement and adjustment is possible at any time, such as, for example a period of low use, for example, midnight. After the measurement is completed, each parameter is adjusted, if necessary, and a result of the measurement and adjustment is fed to the maintenance support apparatus 300 via the communication network 200. In the maintenance support center 300, this result is stored in the apparatus chart information in step 4. When requested by the operator, the result itself and analysis data are transmitted and immediately communicated to the operator. The operator is notified via the display 105. If the software has an analyzing function, an easy to read form of analysis data, such as, for example, graphical representation of the data, may be generated by the software in the MRI apparatus 100.

The scheduled check is linked to its result report. For example, on Friday the scheduled check is performed after the operator sets the phantom according to the request of the software, and the result report is displayed on a display in the hospital on Monday. In addition, email notification may be sent to the operator, an engineer, a chief engineer, etc. automatically.

When the state of apparatus is still poor, the state is classified into the following groups according to the content of the failure and notice the group to the operator. First, use of the MRI apparatus is prohibited completely when the failure may harm the patient or cause a serious damage to the MRI apparatus. Second, when the failure may harm the patient or cause a serious damage to the coil itself, the use of a specific coil is restricted until an alternative coil is prepared. Third, the use of a specific pulse sequence is restricted when the failure may cause an insufficient image. Fourth, the use of a specific imaging method is restricted when the failure may cause a bad image. Additionally, the group of the failure may be displayed on the display in the hospital and may be sent to the operator, the engineer, the chief engineer, etc. by email. When the state of the apparatus is poor, as described above, a request for imaging the phantom in order to confirm the failure may be sent to the operator. This is especially useful for determining failure of the coil.

Figure 4:
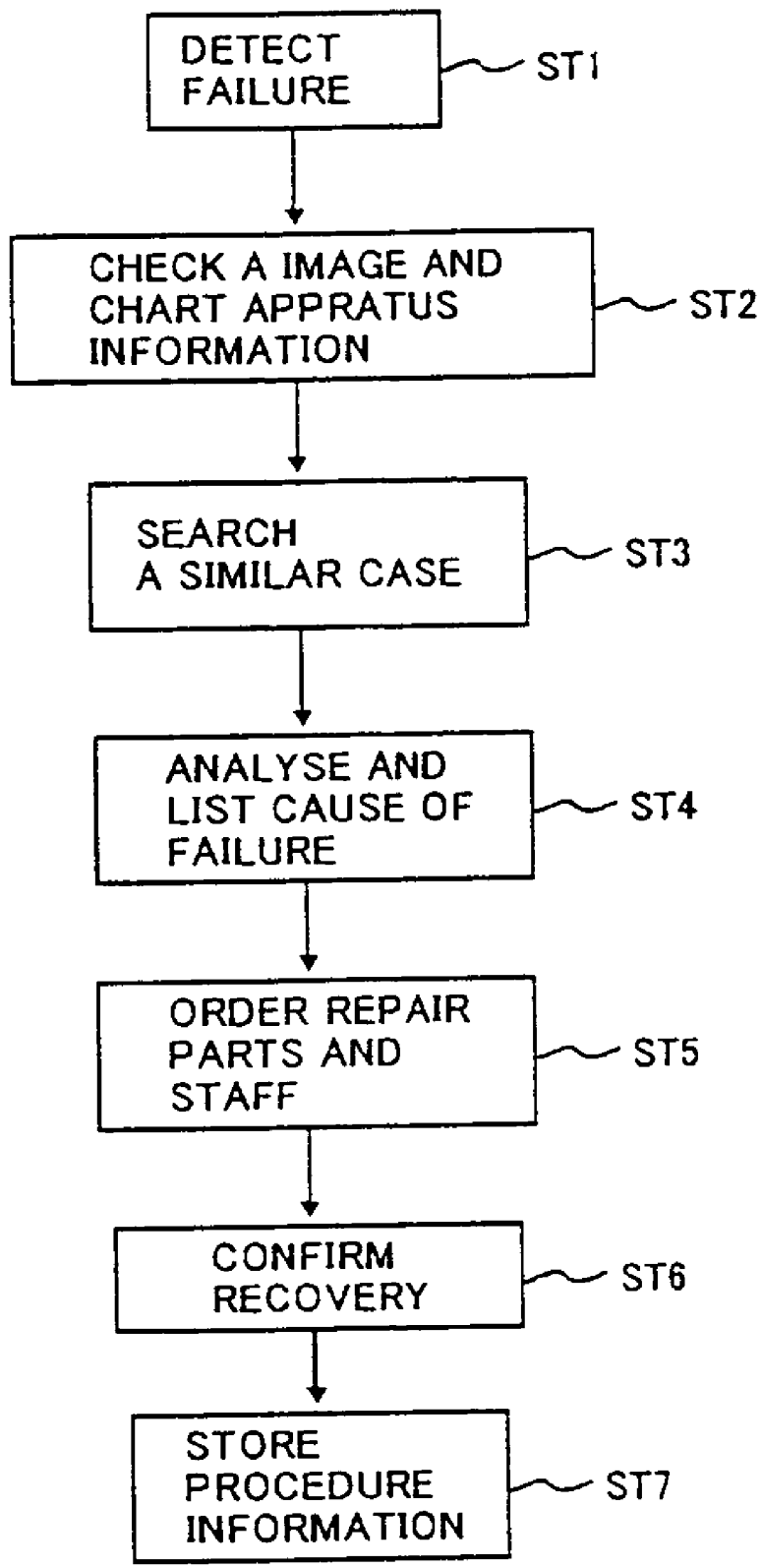
FIG. 4 is a flow chart illustrating operation of an exemplary embodiment of the invention when trouble occurs.

Next, the operation at a failure state will be explained below with reference to FIG. 4. In order to prevent an accident, when the maintenance support apparatus 300 finds a serious error among the error record or a failure image is found by the operator, the maintenance support apparatus 300 receives the failure image and transmits it together with the chart apparatus information to the service center apparatus 400 in step 1.

A troubleshooter in the service center 400 checks the transmitted image and the chart information in step 2 and accesses the chart database 307 in the maintenance support apparatus 300 in order to search for a similar case in step 3. The troubleshooter analyzes the chart and lists possible causes for the failure in order in step 4. The troubleshooter contacts a service provider which supports the hospital, and orders repair parts and staff in step 5. At this time, the troubleshooter or the repair staff of the service provider reports the result of initial investigation and notices expectation of the repair to the operator in the hospital via a communication network, etc. In addition, if failure images were obtained in a similar imaging method in the same MRI apparatus, the troubleshooter may propose that the operator use another imaging method, if possible. Furthermore, if the failure is temporary or can be avoided by an update of the software, the troubleshooter may ask the operator to image the phantom after changing the software in order to confirm that the MRI apparatus has recovered from the failure. The test image of the phantom is transmitted to the service center 400 via the maintenance support apparatus 300 and the troubleshooter can check it and confirm recovery in step 6. The above-mentioned procedure is stored in the database in the maintenance support apparatus 300 to prevent re-failure in step 7.

If the failure is not temporary and repair staff is required, the following procedure may, for example, be performed. The repair parts are ordered based on the cause of the failure, the repair staff of the service provider is requested, the order letter for the repair staff is generated according to the above-mentioned cause list. After these processes are completed, the repair staff contacts the operator. If the spare time data (i.e., times when repairs can be made) is stored in the MRI apparatus in advance by the operator, the repair staff may check it before contact. In such a case, if the failed imaging method is rarely used, the spare time may be given priority. On the other hand, if the failed imaging method is used frequently, the repair staff may request that the operator take a repair time without considering the spare time. The repair staff repairs the MRI apparatus quickly by referring to the apparatus chart information in the maintenance center 300 from the MRI apparatus 100. Additionally, the troubleshooter may ask the operator to image a phantom as mentioned above, before the repair staff comes to the hospital. In this imaging, a pulse sequence where variations of data can be visible by turning off the gradient magnetic field in the phase encoding direction or a pulse sequence where the sensitivity unevenness of FSE can be measured is used, for example.

In the case of repair, the apparatus chart information is of great use. Most troubles are caused by heavy use of the MRI apparatus 300 or adverse environmental conditions, for example, when there is particular problem depending on the hospital. As an example, when moving a large external magnetic object after adjusting the uniformity of the static magnetic field, a pulse sequence which is sensitive to fluctuation of the uniformity, such as EPI and fat control is used. As another example, when another apparatus like an X-ray CT apparatus is being operated and the MRI room is not shielded completely, and a pulse sequence which is sensitive to noise is used. Since it is difficult to collect outside environment data by the MRI apparatus 100, the maintenance support apparatus 300 obtains it cooperating with a hospital and extracts only useful data for repairing. Moreover, the fault can be found more quickly by comparing with other accumulated data from other MRI apparatuses.

Figure 5:
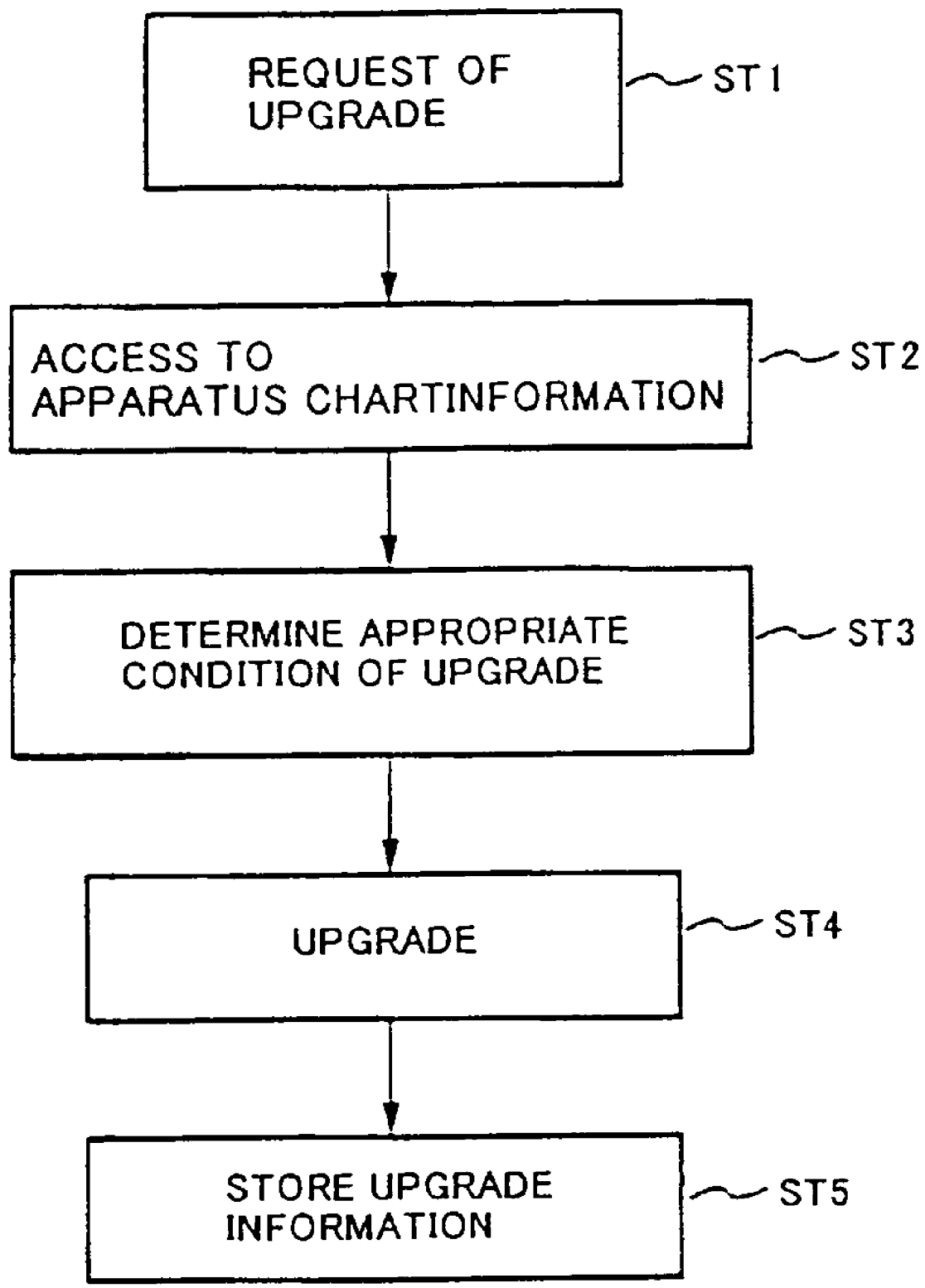
FIG. 5 is a flow chart illustrating operation of an exemplary embodiment of the invention when an MRI apparatus is upgraded.

Next, an upgrade operation will be described below with reference to FIG. 5. For example, when a new highly accurate imaging method (new pulse sequence, etc.) is developed, the MRI apparatus may be upgraded with new software. The upgrade information is stored in the maintenance support apparatus 300 and the operator can check it anytime. If necessary, the operator contacts the maintenance support apparatus 300 via the communication network 200 in step 1. The maintenance support apparatus 300 determines whether the upgrade is appropriate or not. In particular, upgrade staff in the maintenance support apparatus 300 accesses the apparatus chart information in step 2. The staff determines whether the required upgrade is suitable for the MRI apparatus 100 and, if suitable, the appropriate conditions of the upgrade, such as, for example, download speed in step 3. After setting the condition, the maintenance support apparatus 300 sends the upgrade software to the MRI apparatus 100 in step 4. The upgrade information is stored in the chart database 307 in step 5. The MRI apparatus may temporarily use both old and new software until a relation of data measured by both software versions becomes clear. After the evaluation of the relation, only the new software is used.

As another example, the above described apparatus chart information can be used for parts dispatch. In particular, the parts management unit 409 in a service center 400 orders to dispatch parts automatically on basis of the apparatus chart information from the maintenance support apparatus 300.

As described in the above exemplary embodiments, since data input manually by the operator and data measured automatically by the apparatus are consolidated and stored, when the failure occurs, the diagnostic investigation of the MRI apparatus by the operator can be minimized as much as possible or the failure can be prevented in advance.

While the invention has been described in conjunction with specific embodiments thereof, it is evident that many alternatives, modifications and variations will be apparent to those skilled in the art. Accordingly, the exemplary embodiments of the invention, as set forth herein, are intended to be illustrative, not limiting. Various changes may be made without departing from the true spirit and full scope of the invention, as defined in the following claims.

What is claimed is:

1. A system for maintaining and supporting an MRI apparatus, comprising:
   a plurality of MRI apparatuses;
   a maintenance support apparatus for storing data relating to each MRI apparatus;
   a plurality of service center apparatuses, each for supporting maintenance and repair of at least one MRI apparatus; and
   a communication network for providing a communication connection between said MRI apparatuses, said maintenance support apparatus and said service center apparatuses,
   wherein at least one of said MRI apparatuses comprise:
   a memory unit configured to store an imaging schedule used to check a main unit of the MRI apparatus; and
   a controller configured to instruct an operator to prepare images according to the schedule, wherein the controller instructs the operator to prepare a first image for evaluating signal to noise ratio of a whole body coil of the main unit at a first regular interval and a second image for evaluating at least one of an eddy current, FSE adjustment, shimming adjustment, EPI delay time adjustment, FE-EPI time stability, ghost and sensitivity unevenness of FSE at a second regular interval.

2. A system according to claim 1, wherein at least one of said plurality of MRI apparatuses comprise:
   a measurement unit configured to measure at least one parameter of a main unit of an MRI apparatus automatically;
   an input device configured manually input at least one record of the main unit; and
   a memory unit configured to consolidate and store the parameter measured by measurement unit and the manually input data.

3. A system according to claim 2, wherein said parameter includes at least one of an adjustment value, a state value and an error record of the main unit, and said record of the main unit includes at least one of a software and hardware upgrade record, a customized situation record, a network connection record, a repair record, a check record, a maintenance record and an installation record.

4. A system according to claim 1, wherein said data comprises apparatus chart information.

5. A system according to claim 4, wherein said apparatus chart information includes at least one of at least one of an adjustment value, a state value and an error record of the main unit, and a record of the main unit including at least one of a software and hardware upgrade record, a customized situation record, a network connection record, a repair record, a check record, a maintenance record and an installation record.

* * * * *